(12) United States Patent
Eagan

(10) Patent No.: US 6,766,692 B1
(45) Date of Patent: Jul. 27, 2004

(54) PALM-HELD AUTOMOTIVE ACOUSTICAL SENSING DEVICE

(76) Inventor: Christopher S. Eagan, 670 E. Eldorado La., Las Vegas, NV (US) 89123-0508

( * ) Notice: Subject to any disclaimer, the term of this patent is extended or adjusted under 35 U.S.C. 154(b) by 0 days.

(21) Appl. No.: 10/338,947

(22) Filed: Jan. 8, 2003

(51) Int. Cl.$^7$ .............................................. G01N 29/00
(52) U.S. Cl. .......................................... 73/587; 73/649
(58) Field of Search ........................ 73/587, 579, 644, 73/593, 649, 660; 381/56, 58

(56) References Cited

U.S. PATENT DOCUMENTS

| | | | |
|---|---|---|---|
| 5,381,794 A | * 1/1995 | Tei et al. .................... | 600/459 |
| 5,435,185 A | 7/1995 | Eagan | |
| 5,445,026 A | 8/1995 | Eagan | |
| 6,360,607 B1 | * 3/2002 | Charette et al. ............ | 73/587 |
| 6,440,076 B1 | * 8/2002 | Sudol et al. ................ | 600/459 |
| 6,471,649 B1 | * 10/2002 | Saccardo et al. ........... | 600/437 |
| 6,540,685 B1 | * 4/2003 | Rhoads et al. .............. | 600/459 |
| 6,633,820 B2 | * 10/2003 | Bizar .......................... | 702/38 |

* cited by examiner

*Primary Examiner*—Hezron Williams
*Assistant Examiner*—Jacques M Saint-Surin
(74) *Attorney, Agent, or Firm*—A. Mitchell Harris; Jeffrey D. Moy; Weiss, Moy & Harris, P.C.

(57) ABSTRACT

A palm-held acoustical sensing device provides improved accessibility within an engine compartment for sensing engine noise in order to perform diagnostics. Miniaturized electronics are provided within a compact housing that permits free use of the sensing device within an engine compartment, enabling access to engine components that have previously been accessible only with great difficulty. Clamping sensors having wider bandwidth than existing clamping sensors provide improved sensing capability and an electronics and battery housing having one or more sensor input jacks provides for attachment of multiple sensors, improved storage and a lower cost unit providing the advantages of both a flexible shaft sensing unit and a clamping unit.

20 Claims, 4 Drawing Sheets

PALM-HELD AUTOMOTIVE ACOUSTICAL SENSING DEVICE

BACKGROUND OF THE INVENTION

1. Field of the Invention

The present invention relates generally to acoustical sensing devices, and more specifically, to a small palm-held acoustical sensing device for engine diagnostic applications.

2. Background of the Invention

Acoustical sensing devices have been in use for some time for diagnosing engine problems in automotive and other engines. Mechanical failure is generally preceded by operating conditions that generate various noises (e.g., bearing squeal or knocking from loose parts) that can be detected if a sensing device is acoustically coupled to the noise source.

U.S. Pat. No. 5,445,026 "ELECTRONIC INSTRUMENT FOR LOCATING AND DIAGNOSING ENGINE SOUNDS", issued to the inventor of the present invention, describes a first acoustical sensing device having a flexible arm that may be directed toward a noise source within an engine compartment. U.S. Pat. No. 5,435,185 "ELECTRONIC INSTRUMENT FOR LOCATING AND DIAGNOSING AUTOMOTIVE CHASSIS SOUNDS", also issued to the inventor of the present invention, describes a second acoustical sensing device mounted on a clamp and connected via a flexible cable. The first device is useful for quickly scanning reachable engine components and the second device is useful for more permanently attaching a sensor where the first device cannot reach, or where it is desirable to leave the sensor in place for a longer period of time while adjustments are made, for consultation or in order to maintain precise placement of the sensor.

The first (flexible arm) device uses a sensing element that has wide bandwidth for the best sensitivity to the spectrum of noises available. The second (clamping) device uses a sensing element that is durable and easily coupled to the clamping device but has a narrow bandwidth. Both devices are useful for different purposes, as the second device can access locations in an engine compartment that the first cannot, and the first device is sensitive to noises that the second device cannot detect. In particular, it has been noticed that a lower bandwidth can exclude normal engine noise, leaving the operator no level of reference to determine the relative level (and hence importance) of a noise detected by the sensing device.

Therefore, it would be desirable to provide a single low-cost device incorporating the advantages of a clamping device and a device with a flexible shaft. It would be further desirable to provide a clamping device with a wider bandwidth. It would also be desirable to provide a flexible shaft device that improves access to engine compartment locations.

SUMMARY OF THE INVENTION

The above objectives of providing a single low cost device having clamping and flexible shaft device advantages, a clamping device with wider bandwidth and a flexible shaft device with improved access are accomplished in various apparatus in accordance with embodiments of the present invention. A palm-held housing incorporates an amplifier, batteries and volume control, along with an audio jack for connection of headphones and may include one or more input jacks for detachably coupling flexible shaft or clamping sensors. The housing is adapted to fit within the palm of a hand, so that the effective reach of the device with a flexible shaft is greater than the reach of the user's fingers. The clamping device incorporates a condenser microphone coupled to the clamp with an air-tight seal to provide enhanced bandwidth and sensitivity.

The foregoing and other objectives, features, and advantages of the invention will be apparent from the following, more particular, description of the preferred embodiment of the invention, as illustrated in the accompanying drawings.

DETAILED DESCRIPTION OF THE PREFERRED EMBODIMENTS

Figure 1:
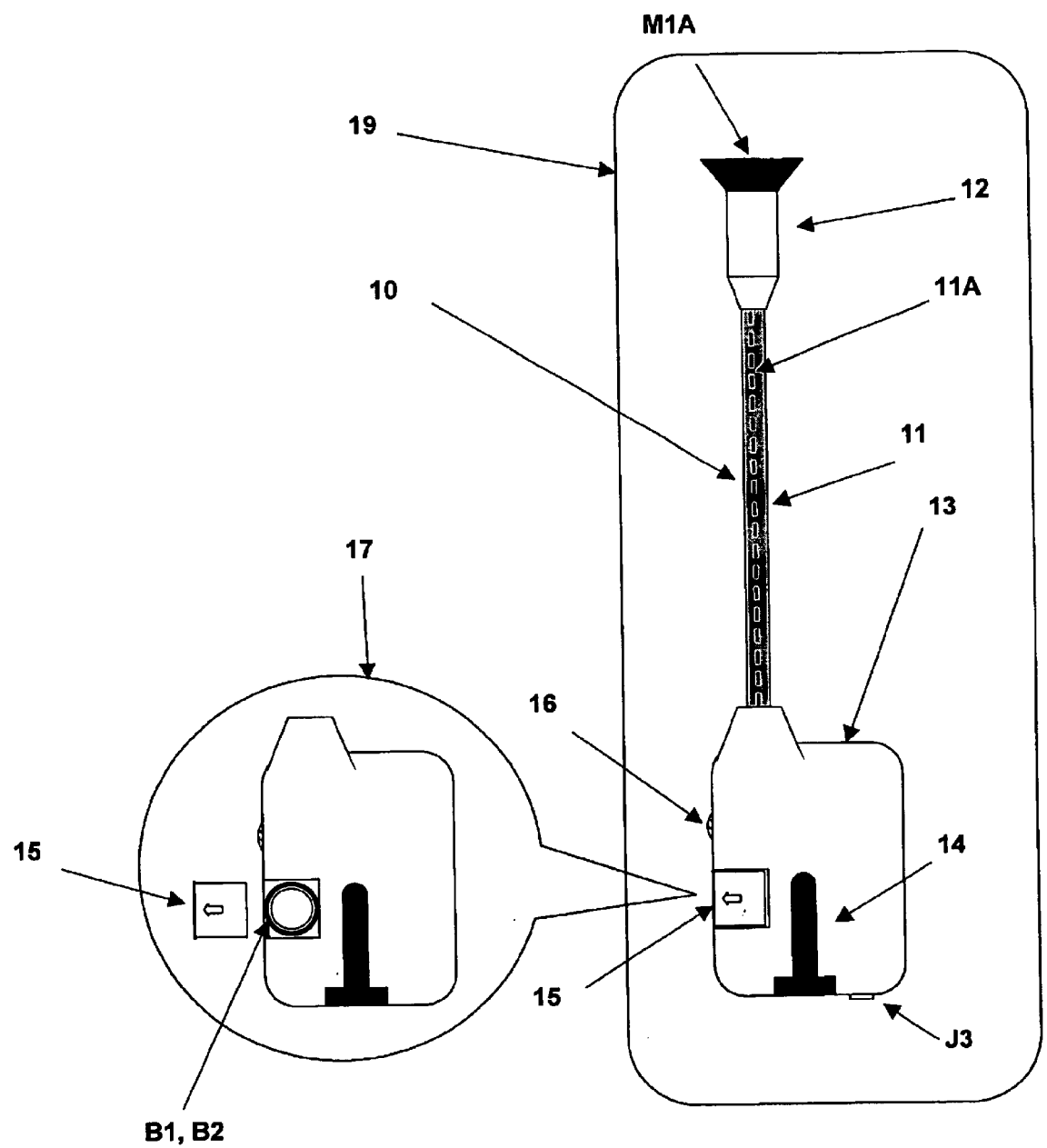
FIG. 1 is a pictorial diagram containing depictions of a palm-held acoustical sensing device in accordance with a first embodiment of the present invention.

Referring now to the figures and in particular to FIG. 1, a palm-held acoustical sensing device 10 in accordance with a first embodiment of the present invention is depicted. A coaxial cable 11 approximately 3 inches long, provides a flexible wiring shaft that couples an acoustical sensor head 12 to an electronics housing 13. Coaxial cable 11 electrically connects the acoustical sensor head 12 to electronics within electronics housing 13 and mechanically connects acoustical sensor head 12 to electronics housing 13. Coaxial cable 11 is generally one having a solid center conductor 11A providing the ability to position acoustical sensor head 12 with respect to electronics housing 13 at different angles, facilitating access to engine compartment components, while also providing a shielded electrical connection to prevent noise from being induced in the interconnecting wiring from external environmental sources. Incorporation of coaxial cable 11, rather than a metal gooseneck having a separate central wiring cable as previously incorporated in automotive sensing devices, provides a low-cost assembly having improved reliability (due to the larger cable and lack of a separate central cable sliding against an internal gooseneck channel). The woven shield of coaxial cable 11 provides superior shielding and mechanical performance over prior gooseneck approaches, as the shield is less permeable to electrical noise, is electrically grounded and conducts less mechanical noise from housing 13 and any vibration sources that are contacted by the outside of coaxial cable 11.

Housing 13 measures approximately 2.0 in×1.0 in by ¼" thick and contains a miniaturized amplifier circuit for amplifying signals received from an acoustical sensing element M1A within sensor head 12, which is a condenser microphone element. A volume control knob 16 is disposed on the outside of housing 13 for controlling the volume of sound provided via an external pair of headphones such as EARBUDS or larger headphones that are attached via connector J3. A battery cover 15 slides away to provide access to batteries B1 and B2, as depicted in callout 17. Batteries B1 and B2 are hearing aid or watch batteries providing for miniaturization of housing 13. A belt clip 14 is provided for temporarily attaching sensing device 10 to a belt or shirt pocket, providing a mechanism for freeing the users hands while sensing device 10 is not in use. A case 19 may be provided for storage of sensing device 10 within a pocket or for general use. Case may be made shorter or smaller by designing the case to hold sensing device 10 with coaxial cable 11 bent so that sensor head 12 is near housing 13. The use of miniaturized electronics, hearing-aid or watch batteries and the reduction of housing 13 and coaxial cable 11 size over existing sensing systems provides for access to components within an engine compartment that were previously inaccessible by such devices. Further, portability and cost are reduced, making sensing device 10 particularly useful to semi-professional mechanics or individuals performing their own automotive diagnosis and repair.

Figure 2:
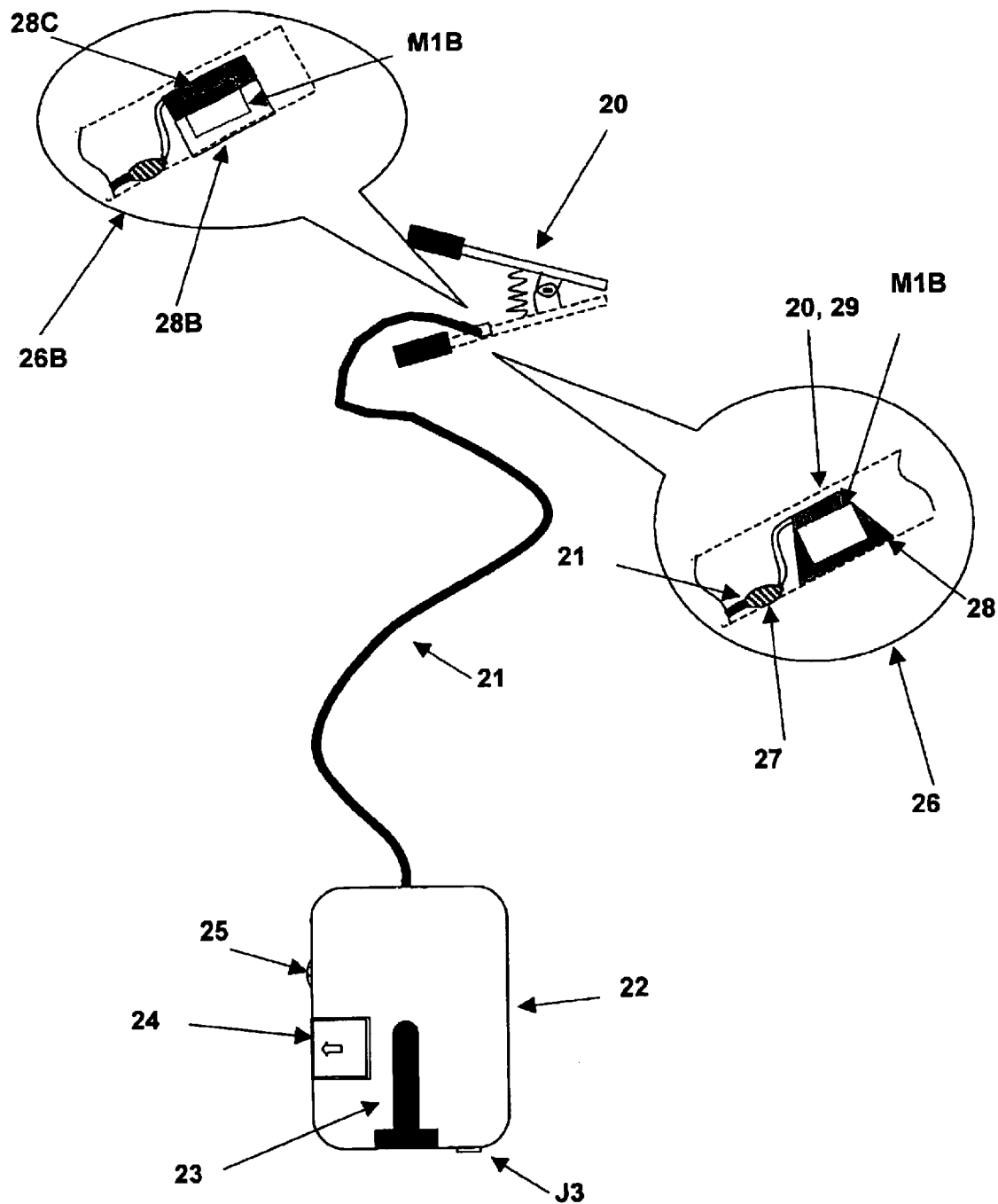
FIG. 2 is a pictorial diagram containing depictions of a palm-held acoustical sensing device in accordance with a second embodiment of the present invention.

Referring now to FIG. 2, an acoustical sensing device in accordance with a second embodiment of the present invention is depicted. A clamping acoustical sensor 20 includes a condenser microphone element M1B. Clamping sensor 20 is used to coupled the acoustical sensing device to engine components, permitting measurement of sound conducted directly from the engine component.

Incorporation of condenser microphone element M1B provides an enhanced performance over previous clamping sensor devices, which use piezoelectric sensors to detect vibrations from the frame 29 of clamp 20. A piezoelectric sensor has a comparatively narrow bandwidth centered around 1 to 4 KHz, which does not permit a clamping acoustical sensing device to sense engine background noise. As a result, while previous clamping devices can detect bearing squeal and other noises that indicate impending failure or defects in an engine component, there is no reference providing a measure of the overall severity of the detected noise.

The sensing device of FIG. 2 overcomes the bandwidth limitations of presently available clamping sensors by incorporating condenser microphone element M1B. However, in order to use a condenser microphone element as a detector for vibrations transmitted through clamp 20 frame 29, is has been determined that an air-tight seal must be employed. Callout 26 depicts one such airtight seal, provided by a bonding agent 28, which may be epoxy, hot-melt glue or other suitable sealing adhesive. Bonding agent 28 is disposed completely around and over condenser microphone element M1B. The active surface of microphone element M1B is facing frame 29, so that the only conducted vibrations sensed by microphone element M1B are those from frame 29 and the other surfaces of microphone element M1B are likewise sealed off from air-convection transmitted vibration, as in general condenser microphone element M1B is sensitive to air pressure changes on all surfaces and therefore must be completely isolated. A second adhesive 27 may be used to attach cable 21 to frame 29 or bonding agent 28 may be disposed over both microphone element M1B and one end of cable 21.

Similarly to the embodiment of FIG. 1, the embodiment of FIG. 2 includes a palm-sized housing 22 containing miniaturized electronics. Housing 22 includes a belt clip 23 for holding the housing while clamp 20 is in use or for temporary storage. Volume control knob 25 and battery cover 24 are disposed at the side of housing 22 and headphone connector J3 is disposed at an end of housing 22, and providing similar functions to corresponding elements of FIG. 1 as described above.

Callout 26B depicts an alternative airtight seal that may be incorporated within an embodiment of the present invention. Rubber (or other flexible material) gasket 28B isolates air from the active surface of microphone element M1B by providing a tight slip-fit connection to microphone element M1B enclosure. The back of microphone element M1B is covered by a back cover 28C substantially sealing microphone element M1B from outside air-conducted acoustical vibration. Gasket 28B may be adhered to frame 29 or may include a shoulder that is press-fit through a hole in frame 29.

Figure 3A:
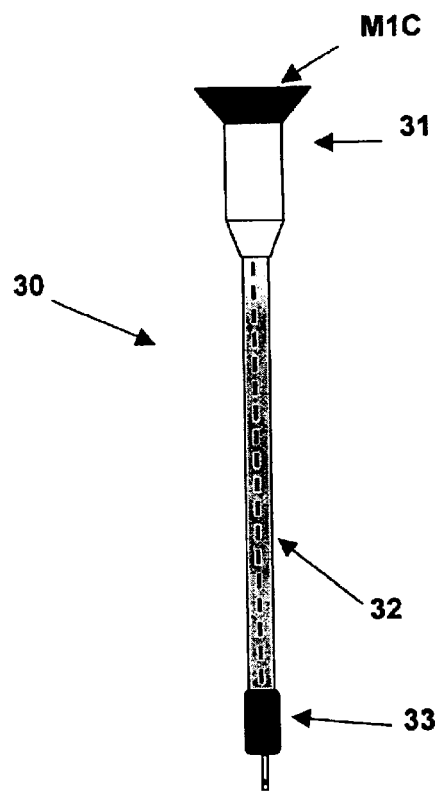
FIGS. 3A–3C are pictorial diagrams containing depictions of components of palm-held acoustical sensing devices for configuration in accordance with other embodiments of the present invention.
Figure 3B:
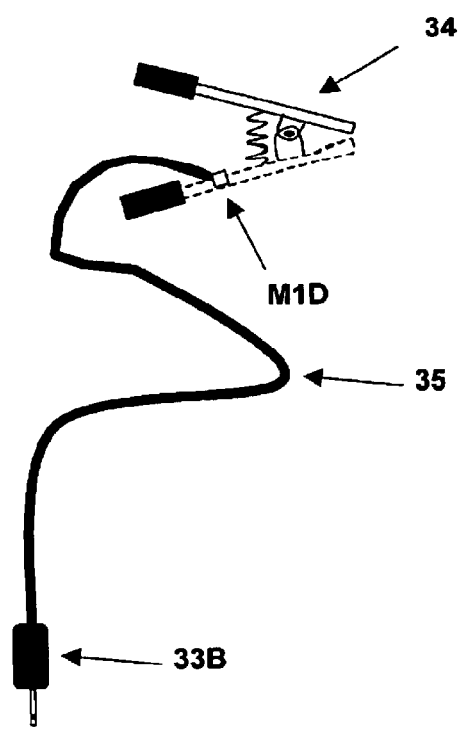
Figure 3C:
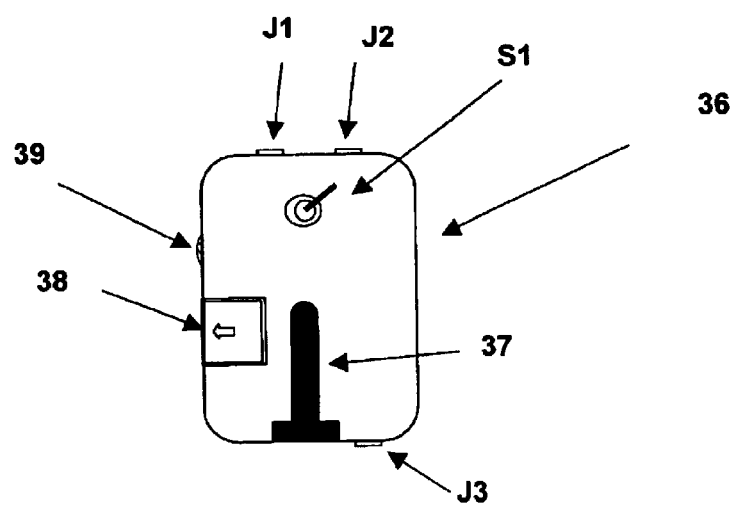

Referring now to FIGS. 3A–3C, components of an acoustical sensing device that may be combined to form various embodiments of the present invention are depicted. FIG. 3A depicts a detachable sensor assembly 30 including a coaxial cable 32 with a sensor head 31 disposed at a first end of coaxial cable 32 and having an acoustical sensor M1C incorporated therein. A male audio connector 33 provides a means for detachably coupling sensor assembly 30 to a housing 36 as depicted in FIG. 3C. Housing 36 includes two or more female connectors J1 and J2 for attaching acoustical sensors to housing 36. A switch S1 provides for selection among acoustical sensors inserted in connectors J1 and J2 and generally will be used for switching between two clamping type sensors, although combinations of clamping and flexible shaft sensors may be attached. Housing 36 encloses the miniaturized electronics described above (with the addition of switch S1 and additional input connectors J1 and J2). Housing similarly includes headphone connector J3, volume control knob 39, battery cover 38 and belt clip 37.

A clamping device adapted for use with housing 36 is depicted in FIG. 3B. Clamping device includes condenser microphone element M1D attached to a clamp 34 with an airtight seal, a cable 35 and a male connector 33B electrically coupled to microphone element M1D, so that microphone element M1D is selectable by switch S1 when connector 33B is inserted into one of connectors J1 and J2 on housing 36.

Figure 4:
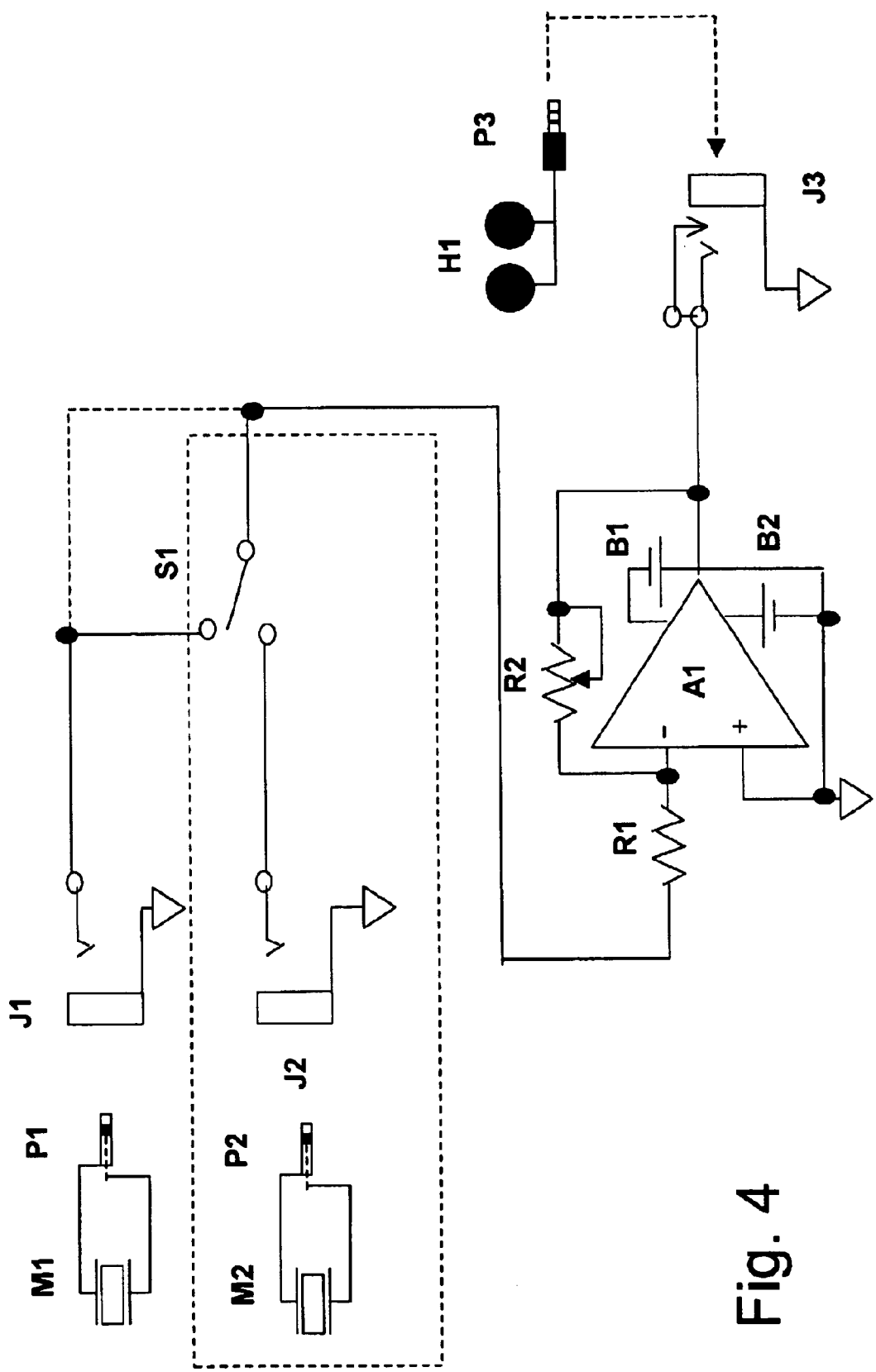
FIG. 4 is an electronic schematic depicting the amplifier, batteries and connectors disposed within the housings of FIGS. 1, 2, and 3C in accordance with the various disclosed embodiments of the invention.

Referring now to FIG. 4, miniaturized electronics as incorporated in the various above-described embodiments of the present invention are depicted. Acoustical sensing element M1 (and optionally second acoustical sensing element M2) are connected to plug P1 (and optional plug P2). Jack J1 provides for connection of plug P1 and optional jack J2 provides for connection of plug P2. Jacks J1 and J2 are connected to switch S1 which selects among sensors connected to jacks J1 and J2 and provides the signal from the selected device to amplifier A1 via resistor R1. If only one sensor is used (as depicted in the embodiments of FIGS. 1 and 2), then jacks J1 and 32, P1 and P2 and switch S1 are not needed and the sensor signal is connected directly to resistor R1. Resistor R2 is connected to amplifier A1 and is a variable resistor for setting the gain of the headphone amplifier A1, and is mechanically coupled to the various volume knobs depicted in FIGS. 1–3.

Amplifier A1 may be a low-voltage high-current op-amp, or a special low voltage headphone amplifier integrated circuit, or a device fabricated with discrete transistors. While depicted as a differential amplifier configured for a single-ended input, amplifier A1 may receive a differential signal from acoustical sensors (with appropriate wiring and connector changes) or amplifier A1 may be a single-ended amplfier. Batteries B1 and B2 provide power to amplifier A1 and headphone jack J3 is connected to the output of amplifier A1 to provide a signal to headphones H1 via connection of headphone plug P3 to jack J3.

While the invention has been particularly shown and described with reference to the preferred embodiments thereof, it will be understood by those skilled in the art that the foregoing and other changes in form, and details may be made therein without departing from the spirit and scope of the invention.

What is claimed is:

1. An acoustical sensing device, comprising:
   a clamp for temporary attachment to an engine component whereby vibrations from said engine component are conducted to a frame of said clamp;
   a condenser microphone element mechanically coupled to said clamp via an airtight seal completely covering said microphone element, whereby said condenser microphone element responds substantially only to said conducted vibrations from said frame of said clamp;
   an amplifier circuit having an input coupled to said condenser microphone and an output coupled to an audio connector for connection to an external pair of headphones;
   one or more batteries coupled to a power supply of said amplifier; and
   a housing for enclosing said amplifier circuit, said batteries and said connector.

2. The acoustical sensing device of claim 1, wherein said airtight seal is provided by a bonding material completely surrounding said condenser microphone element and extending to said frame of said clamp, whereby said bonding material prevents flow of air to and from any surface of said condenser microphone element.

3. The acoustical sensing device of claim 2, wherein said bonding material is an epoxy resin.

4. The acoustical sensing device of claim 2, wherein said bonding material is a hot-melt glue.

5. The acoustical sensing device of claim 1, wherein said airtight seal is provided by a flexible gasket mechanically attached to said frame and having an inner void portion for receiving said condenser microphone element, and a back cove applied over a back of said condenser microphone element.

6. The acoustical sensing device of claim 1, wherein said housing is detachably coupled to said clamp via a connector disposed on a surface of said housing, said connector having electrical terminals coupled to said amplifier, and a mating connector electrically connected to a cable electrically coupled to said condenser microphone element.

7. The acoustical sensing device of claim 1, wherein said housing is substantially rectangular, adapted to fit within the palm of a human hand, and has outside dimensions less than or equal to 0.5 in by 2.0 in by 2.0 in, whereby said housing does not impede accessibility of said human hand within said engine compartment.

8. A palm-held acoustical sensing device, comprising:
   a flexible wiring shaft having an acoustical sensor disposed at a first end for directing at noise sources within an engine compartment;
   an amplifier circuit having an input coupled to said acoustical sensor and an output coupled to a connector for connection to an external pair of headphones;
   one or more batteries coupled to a power supply of said amplifier;
   a housing for enclosing said amplifier circuit, said batteries and said connector, wherein said housing is substantially rectangular, adapted to fit within the palm of a human hard, and has outside dimensions less than or equal to 0.5 in by 2.0 in by 2.0 in, whereby said housing does not impede accessibility of said human hand within said engine compartment, and wherein said flexible wiring shaft is connected to said housing at a second end of said flexible wiring shaft and wherein said flexible wiring shaft includes wiring disposed within said flexible wiring shaft for connecting said acoustical sensor to said input of said amplifier.

9. The palm-held acoustical sensing device of claim 8, wherein said flexible wiring shaft has an axial length of less than four inches, whereby said palm-held acoustical sensing device can be easily fit into a typical shirt pocket.

10. The palm-held acoustical sensing device of claim 9, further comprising a substantially rectangular case for storing an assembly comprising said flexible wiring shaft and said housing, said case having outside dimensions less than or equal to 2.0 in by 1.0 in by 6.0 in, whereby said acoustical sensing device is protected while placed in said pocket.

11. The palm-held acoustical sensing device of claim 8, further comprising a belt clip disposed on a side of said housing for temporarily clipping said acoustical sensing device to a belt, pocket or other article of clothing.

12. The palm-held acoustical sensing device of claim 8, wherein said flexible wiring shaft is detachably coupled to said housing via a connector disposed on a surface of said housing, said connector having electrical terminals coupled to said amplifier, and a mating connector electrically connected to a cable disposed within said flexible wiring shaft and electrically coupled to said acoustical sensor.

13. The palm-held acoustical sensing device of claim 8, wherein said acoustical sensing device is a condenser microphone element.

14. The palm-held acoustical sensing device of claim 8, wherein said flexible wiring shaft is a coaxial cable segment providing mechanical connection of said acoustical sensor to said housing and electrical connection of said acoustical sensor to said amplifier circuit.

15. An acoustical sensing device, comprising:
   at least two acoustical sensors for sensing engine compartment noise;
   a switch coupled to said at least two acoustical sensors for selecting among said at least two acoustical sensors; and
   an amplifier circuit having an input coupled to said switch and an output coupled to a fourth audio connector for connection to an external pair of headphones, whereby an audible representation of said engine component noise detected by a selected one of said at least two acoustical sensors is provided by said headphones.

16. The acoustical sensing device of claim 15, further comprising:
   at least two male connectors each connected to a corresponding one of said at least two acoustical sensors;
   a housing for enclosing said amplifier circuit;
   at least two female connectors disposed on a side of said housing and electrically coupled to said switch for detachably coupling said acoustical sensors to said switch.

17. The acoustical sensing device of claim 16, wherein at least one of said at least two acoustical sensors is mounted to a flexible wiring shaft, wherein said at least one acoustical sensor is disposed at a first end of said flexible wiring shaft for directing at noise sources within an engine compartment and wherein said male connector corresponding to said at least one acoustical sensor is disposed at a second and of said flexible wiring shaft.

18. The acoustical sensing device of claim 17, wherein said flexible wiring shaft has an axial length of less than four inches, whereby said at least one acoustical sensor can be easily fit into a typical shirt pocket.

19. The acoustical sensing device of claim 15, wherein at least one of said at least two acoustical sensors comprises:
   a clamp for temporary attachment to an engine component whereby vibrations from said engine component are conducted to a frame of said clamp; and
   a condenser microphone element mechanically coupled to said clamp via an airtight seal over an active surface of said microphone element, whereby said condenser microphone element responds substantially only to said conducted vibrations from said frame of said clamp.

20. The acoustical sensing device of claim 15, further comprising a housing for enclosing said amplifier circuit, wherein said housing is substantially rectangular, adapted to fit within the palm of a human hand, and has outside dimensions less than or equal to 0.5 in by 2.0 in by 2.0 in, whereby said housing does not impede accessibility of said human hand within said engine compartment.

* * * * *